United States Patent [19]

Mechoulam et al.

[11] 4,179,517

[45] Dec. 18, 1979

[54] NOVEL TETRAHYDROCANNABINOL TYPE COMPOUNDS

[75] Inventors: Raphael Mechoulam, Jerusalem; Naphtali Lander, Tel-Aviv; Shabtay Dikstein; Benyamin Shalita, both of Jerusalem, all of Israel

[73] Assignee: Yissum Research Development Company of the Hebrew University of Jerusalem, Jerusalem, Israel

[21] Appl. No.: 755,083

[22] Filed: Dec. 28, 1976

[30] Foreign Application Priority Data

Jan. 12, 1976 [IL] Israel ........................................ 48824

[51] Int. Cl.² ................... A61K 31/35; C07D 311/02
[52] U.S. Cl. .................................. 424/283; 260/345.3
[58] Field of Search ............................. 424/283, 287; 260/345.3

[56] References Cited

U.S. PATENT DOCUMENTS 4,025,516  5/1977  Razdan et al. ..................... 260/345.3

OTHER PUBLICATIONS

Mechoulam et al., JACS, 94, 6159 (1972).
Jen et al., JACS, 89, 4551 (1967).
Mechoulam et al., JACS, 89, 4552 (1967).
Mechoulam et al., JACS, 87, 3273 (1965).
Yaoni et al., JACS, 86, 1646 (1964).
Fahrenholtz et al., JACS, 89, 5934 (1967).
Taylor et al., JACS, 88, 367 (1966).

*Primary Examiner*—Nicky Chan
*Attorney, Agent, or Firm*—Browdy and Neimark

[57] ABSTRACT

A pharmaceutical composition of matter substantially devoid of "cannabis-type" CNS activity containing as active ingredient a compound of the formula

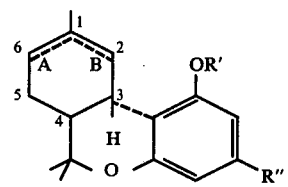

wherein A-----B designates a 1(2) or a 6(1) double bond and wherein R' designates —H or —CO—R where R is lower alkyl, and R" designates alkyl and novel compounds of the 3S,4S configuration of the formula

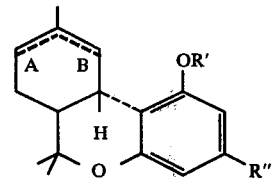

wherein A----B designates a 1(2) or a 6(1) double bond, R' designates hydrogen or —CO—R where —R is lower alkyl, and R" designates alkyl of at least 6 carbon atoms.

15 Claims, No Drawings

NOVEL TETRAHYDROCANNABINOL TYPE COMPOUNDS

The present invention relates to certain novel tetrahydrocannabinol (THC) type compounds and to pharmaceutical compositions of matter containing same as active ingredients. More specifically, the present invention relates to novel THC type compounds which are characterized by an absolute stereochemistry at the positions 3 and 4 of the molecule which is opposite to that of the configuration in the natural series, i.e., whereas it is 3R,4R in the natural series, it is 3S,4S in the compounds of the present invention. The novel compounds of the present invention are characterized by certain specific and quite unexpected pharmaceutical properties and thus they are useful as active ingredients of novel pharmaceutical compositions of matter. In the corresponding natural compounds of the 3R,4R configuration there exists a very pronounced psychotropic "cannabis" type effect and this is very undesirable for well-known reasons. This effect precludes the use of such compounds for other therapeutically interesting effects, as the cannabis-effect is so pronounced and deleterious, that such compounds cannot be used. According to the present invention there are provided novel compounds wherein the undesired "cannabis" effect is practically eliminated, and which compounds can be used for the treatment of various diseases and disorders, as will be set out in greater detail hereinafter.

The pharmaceutically active compounds which are active ingredients of the novel pharmaceutical preparations are of the general formula

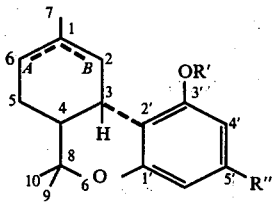

wherein A------B designates a 1(2) or a 1(6) double bond and wherein R' designates —H or —CO—R where R is lower alkyl, and R" designates alkyl.

The compounds wherein R" has 1,2,3,4,6 or more carbon atoms are novel per se.

The nomenclature given above is that of the terpene series. The same compound according to the C.A. nomenclature is:

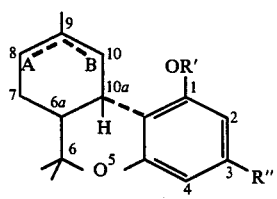

The main psychotropically active compounds present in *Cannabis sativa* or in its preparations (marijuana, hashish, etc.) is (3R,4R)-(−)-Δ¹-THC (I). Occasionally small quantities of the compound (3R,4R)-(−)-Δ⁶-THC (II) are found. Both compounds have a pronounced activity on mammals and on humans, producing the typical "cannibis" effect. This effect can be measured in animals in a quantitative manner by various tests, two of these being the monkey test, Grunfeld et al., Psychopharmacol. 14, 200 (1969) and by the ring test, Pertwee, Brit. J. Pharmacol. 46, 753 (1972). In the monkey test the minimum giving an effect is 50 γ/kg of the (3R,4R)-(−)-Δ¹-THC while that of (3R,4R)-(−)-Δ⁶-THC is 0.1 to 0.25 mg/kg.

In the ring test the above compounds are active at less than 1 mg/kg. There have been prepared various derivatives of the above compounds, having various different side-chains, see "Marijuana, Chemistry, Pharmacology, Metabolism and Clinical Effects," R. Mechoulam (ed.), Academic Press, New York, 1973. Many of these possess the activity of the natural compounds, frequently at lower dosages and of longer duration, such as in the monkey test, 24 hours instead of 4 hours with the 1", 2"-(dimethylheptyl) homologue of (3R,4R)-(−)Δ¹-THC (III). The corresponding Δ⁶-THC compound (IV) acts at 0.5 mg/kg for 30 hours.

Various cannabinoids, both natural and synthetic, have been examined for their therapeutic activity, see Ann. Rev. Pharmacol. 15, 210 (1975) and Ann. Rep. Med. Chem. 9, 253 (1974). These have shown that such compounds have a potential activity useful in the treatment of disorders such as glaucoma, high blood pressure, states of anxiety, insomnia, allergy, asthma, epilepsy, nausea, ulcers, pain (including migraine), etc. Due to the strong cannabis-type psychotropic activity of these compounds, which is a very pronounced and undesired side-effect, there is no possibility to make use of the useful pharmacological properties of the above defined compounds in view of the cannabis-type effects.

The novel compounds according to the present invention are substantially devoid of the undesired cannabis-type effects and can be used for the treatment of various diseases and disorders without undesired side-effects. As stated above, the novel compounds have an absolute stereochemistry at the 3- and 4-positions (terpene nomenclature) opposite to that of the natural series, i.e., they have a (3S,4S)-configuration. The compounds have a (+)-rotation of an absolute value approximately equal to that of the corresponding (−)-series compound.

For example, the 1",2"-(dimethylheptyl)-homologue of (+)-(3S,4S)-Δ⁶-THC(Va) shows no activity in the monkey test up to 5 mg/kg. When tested on glaucomatic rabbits this compound is active in dilutions lower than 0.001% when administered directly into the eye in suspension. It has also a pronounced anti-ulcer activity. It is effective in the prevention and reduction of desoxycorticosterone and salt induced hypertension.

The novel compounds of the present invention were tested by the following tests:
1. Intestinal motility according to Chester et al., Brit. J. Pharmac. 49, 588 (1973);
2. Prevention of DOCA induced hypertension according to Ben-Ishay et al., Experientia, 28, 1321 (1972); Reduction of such hypertension was achieved by administering the substance to hypertensive rats, for a period of three weeks.
3. Antiglaucomatic effect on glaucoma of rabbits. The glaucoma is produced by administration of α-chymotrypsin into the eye. After four weeks about 25% of the rabbits develop stable glaucoma.
4. CNS-activity according to the "Ring test", see above;

5. CNS-activity according to the "Monkey test", see above;
6. Body temperature by rectal thermistor probe;
7. Ulcer prevention according to Aarsen, Arzneim. Forschung, 23. 1346 (1973).

Two THC-type compounds with (3S,4S) stereochemistry have been reported hitherto in literature, see Mechoulam: Marijuana, Chemistry, Pharmacology, Metabolism and Clinical Effects, Academic Press 1973. It has been shown that these two, (+)-$\Delta^1$-THC (Compound VI) and (+)-$\Delta^6$-THC (Compound VII) have a low cannabis-type activity. Nothing has been published about other pharmacological properties of these, and no such activity could be predicted.

The synthesis of the novel compounds according to the present invention is conveniently effected by acid condensation of trans-(+)-verbenol (VIII) or of cis-verbenol (IX) with a 5-alkyl resorcinol, wherein the alkyl group is different from $C_5H_{11}$. When p-toluene sulfonic acid was used the corresponding (+)-5-alkyl-2-(2-pinene-4-yl)-resorcinol (X) was obtained as main product of the reaction. This intermediate was subsequently converted by treatment with boron trifluoride-ethereate to the corresponding (3S,4S)-(+)-$\Delta^6$-THC homologue (cfV). The corresponding (3S,4S)-(+)-$\Delta^1$-THC homologues (XI) were prepared by reacting compound V with gaseous hydrogen chloride in the presence of zinc chloride in a toluene solution, giving the XIII intermediate, which latter was dissolved in dry benzene and reacted with a suitable base, such as dry potassium-tert-amylate, to give the desired compound XI. The dehydrochlorination can also be effected with other bases, such as sodium hydride.

When the reaction is effected with boron trifluoride instead of p-toluene sulfonic acid, the (3S,4S)-(+)-$\Delta^6$-THC homologue can be obtained directly, but in lower yields than in the above two-step synthesis.

The above compounds can be easily converted to the corresponding esters, the esterification being effected by conventional means.

The following examples are intended to illustrate the present invention, and these are to be construed in a non-limitative manner. It is clear that various modifications in the process of the invention and in the choice of reactants can be resorted to without departing from the scope of the present invention.

The following Table illustrates the compounds mentioned, while List A gives the names of these according to the C.A. nomenclature.

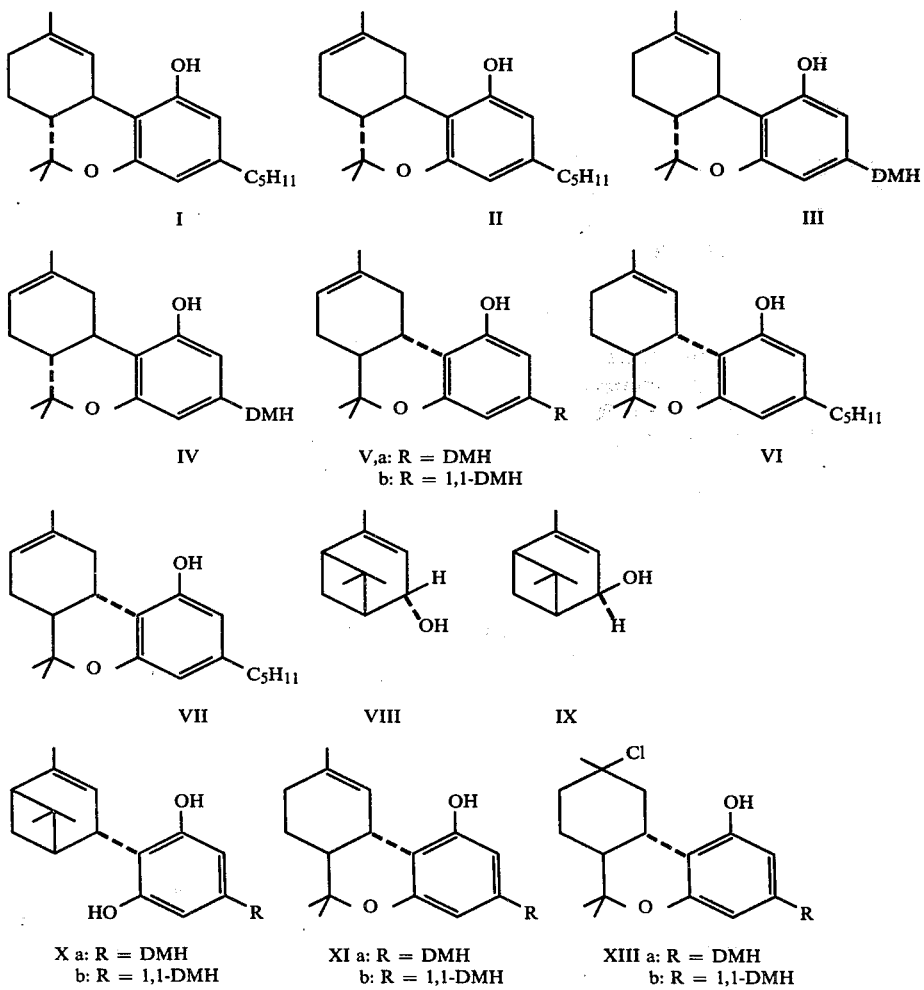

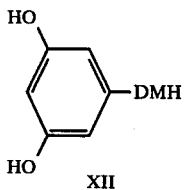

DMH = 1,2-dimethylheptyl

Appendix A. Chemical Abstract names of compounds.

(Underlined names according to the terpene nomenclature)

(3R,4R)-(−)-Δ¹-THC (I): 6aβ, 7, 8, 10aα, tetrahydro-6,6,9-trimethyl-3-pentyl-(−)-6H-dibenzo [b,d] pyran-1-ol.

(3R,4R)-(−)-Δ⁶-THC (II): 6aβ, 7, 10, 10aα tetrahydro-6,6,9-trimethyl-3-pentyl-(−)-6H-dibenzo [b,d] pyran-1-ol.

1″,2″-dimethylheptyl homolog of (3R,4R)-(−)-Δ¹THC (III):

6aβ, 7, 8, 10a, tetrahydro-6,6, 9-trimethyl-3-(1,2-dimethylheptyl)-(−)-6H=dibenzo [b,d] pyran-1-ol.

1″,2″-dimethylheptyl homolog of (3R,4R)-(−)-Δ⁶-THC (IV):

6aβ, 7, 10, 10aα tetrahydro-6,6,9-trimethyl-3-(1,2-dimethylheptyl)-(−)-6H-dibenzo [b,d] pyran-1-ol.

1″,2″-dimethyl heptyl homolog of (3S,4S)-(+)-Δ⁶-THC (Va):

6aα, 7, 10, 10aβ tetrahydro-6,6,9-trimethyl-3-(1,2-dimethylheptyl)-(+)-6H-dibenzo [b,d] pyran-1-ol.

(3S,4S)-(+)-Δ¹-THC (VI): 6aα, 7, 8-10aβ tetrahydro-6,6,9-trimethyl-3-pentyl-(+)-6H-dibenzo [b,d] pyran-1-ol.

(3S,4S)-(+)-Δ⁶-THC (VII): 6aα, 7, 10, 10aβ tetrahydro-6, 6, 9-trimethyl-3-pentyl-(+)-6H-dibenzo [b,d] pyran-1-ol.

1″,2″-dimethylheptyl homolog of (3S,4S)-(+)-Δ¹-THC (XIa):

6aα, 7, 8-10aβ, tetrahydro-6, 6, 9-trimethyl-3-(1,2-dimethylheptyl)-(+)-6H-dibenzo [b,d] pyran-1-ol.

EXAMPLE 1

(+)-5-(1,2-Dimethylheptyl)-2-(2-pinene-4-yl-resorcinol. (Compound Xa). Verbenol (trans, $[\alpha]_D+112°$)-(VIII) (4.56 g) in dry chloroform (100 ml) was added over a period of 30 min to a solution of 5-(1,2-dimethylheptyl)-resorcinol (XII) (7.08 g) and p-toluene sulphonic acid (0.6 g) in chloroform (800 ml). The solution was left at room temperature for a further 30 min. washed with a saturated solution of sodium bicarbonate, dried and evaporated. The oil obtained (12.5 g) was chromatographed on Florisil (650 g.). Elution with petroleum ether-ether in a ratio of 96:4 gave Xa (8.81 g), $[\alpha]_D+80°$ (in ethanol); u.v. spectrum (in ethanol) 271 mμ(ε, 500), 278 (ε, 510); n.m.r. spectrum (in CCl₄) 6.02, 5.72, 3.93, 1.88, 1.32, 0.98, 0.88, 0.78, 0.68 ppm. Analysis: $C_{25}H_{38}O_2$ requires C, 81.03; H, 10.34. Found: C, 80.88; H, 10.38.

The same reaction can also be undertaken with cis-verbenol (compound IX).

EXAMPLE 2

(+)-Δ⁶-THC, dimethylheptyl homolog; C.A. name: 6aα,7, 10, 10aβ, Tetrahydro-6,6,9-trimethyl-3-(1,2-dimethylheptyl)-(+)-6H-dibenzo[b,d] pyran-1-ol (compound Va). —The above described compound Xa (8.41 g) was dissolved in dry methylene chloride (200 ml) (distilled over calcium hydride). Boron tri fluoride etherate (8.5 ml) was added. The solution was stirred for 10 min. under nitrogen. The solution was diluted with ether and washed with a solution of sodium bicarbonate. The organic phase was washed with water, dried over magnesium sulphate and the solvent evaporated. The oil obtained (8.1 g) was chromatographed on Florisil (810 g). On elution with petroleum ether-ether (in a ratio of 0.5:100) compound Va was obtained as an oil, $[\alpha]_D+225°$ (ethanol). Analysis: $C_{25}H_{38}O_2$ requires C, 81.03; H, 10.34. Found: C, 80.85; H, 10.48. Boiling point: 140°–150° C. 0.001 mmHg. Ultra violet spectrum: 273 mμ(ε, 1150), 280 (ε, 1220). N.m.r. (in CCl₄), δ: 6.12 (1H), 5.92 (1H), 5.35 (1H), 3.19 (1H), 1.66, 1.35, 1.09 (methyl groups), 0.87, 0.77, 0.66 (split methyl groups). Compound Va can also be directly prepared from 5-(1,2-dimethylheptyl)-resorcinol (XII) and verbenol. Thus (+)-trans-verbenol (300 mg) (VIII) and XII (470 mg) were dissolved in 25 ml methylene chloride. Boron trifluoride etherate (0.25 ml) was added. The reaction mixture was kept under nitrogen for 2 hr and then at room temp. of ½ hr after which it was washed with sodium bicarbonate, dried and evaporated. The oily residue was chromatographed on Florisil (45 g). The main fraction (eluted with petroleum ether-ether, ratio 100:0.5) (0.5 g) was shown to identical with compound Va.

The acetate of compound Va was prepared by dissolution 1 gr of Va in 10 ml of pyridine and addition of acetic anhydride (2 ml). The mixture was left at room temperature for 12 hrs, the solvents were evaporated and the acetate of V was distilled at 150° C. at 0.001 mmHg.

EXAMPLE 3

(+)-Δ¹-THC, dimethylheptyl homolog. CA name: 6aα, 7, 8, 10aβ-Tetrahydro-6,6,9-trimethyl-3-(1,2-dimethylheptyl)-(+)-6H-dibenzo[b,d]pyran-1-ol (compound XIa). Compound Va (2.30 g) was dissolved in dry toluene (200 ml). Zinc chloride (0.45 g) was added. Dry gaseous hydrochloric acid was bubbled through the mixture, for 6 hr. The temperature of the reaction mixture was kept at −15° C. The reaction mixture was then diluted with ether and washed with water several times. The solution was dried and evaporated to give 6aα, 7, 8, 9, 10, 10aβ-hexahydro-6,6,9-trimethyl-9-chloro-3-(1,2- dimethylheptyl)-(+)-dibenzo[b,d]pyran-1-ol (compound XIIIa), $[\alpha]_D+80$ (CHCl$_3$). U.v. spectrum 276 m$\mu$($\epsilon$ 1240), 279 m$\mu$($\epsilon$, 1270).

Compound XIIIa (2.54 g) was dissolved in dry benzene (10 ml) and was added to dry potassium-tert-amylate prepared from tert-amyl alcohol (20 ml). The reaction was stopped after 5 hrs. Benzene (50 ml) was added, then the solution was washed with water till the ph was 7, the organic phase was dried and evaporated to give an oily residue (2.3 g). It was chromatographed on Florisil (700 gr). Elution with petroleum ether-ether in a ratio of 100:0.5 gave compound XIa (1.01 gr), $[\alpha]_D+120°$, u.v. spectrum 273 m$\mu$ ($\epsilon$ 1980), 279 m$\mu$ ($\epsilon$, 2010), n.m.r. (in CCl$_4$) 6.31 (1H), 6.10 (1H), 5.95 (1H), 3.12 (1H), 1.65, 1.40, 1.20, 1.06, 0.87, 0.75, 0.65.

Analysis: $C_{25}H_{38}O_2$ requires C, 81.03; H 10.34. Found: C, 80.82; H, 10.42. Compound XIa distills at 150° C. at 0.001 mmHg.

Other bases, such as sodium hydride, can also be employed for the dehydrochlorination.

EXAMPLE 4

In the procedures of example 1 and 2, using the following 5-alkyl resorcinols in place of 5-(1,2-dimethylheptyl)-resorcinol, 5-(1,2-dimethyloctyl) resorcinol
5-(1,2-dimethylhexyl) resorcinol
5-(1,1-dimethylheptyl) resorcinol
5-(1-ethyl-2-methylpropyl) resorcinol
5-(methylnonyl) resorcinol
5-(1-methyloctyl) resorcinol
5-(1,2,4-trimethylhexyl) resorcinol
5-(1-ethylheptyl) resorcinol the corresponding (+)-5-alkyl-2-(2-pinene-4-yl)-resorcinols (X) and 6a$\alpha$,7, 10, 10a$\beta$, tetrahydro-6,6,9-trimethyl-3-alkyl-(+)-6H-dibenzo[b,d] pyran-1-ol analogs (V) were obtained, from which by the procedure of example 3 the corresponding 6a$\alpha$, 7, 8, 9, 10, 10a$\beta$-hexahydro-6,6,9-trimethyl-9-chloro-3-alkyl-(+)-dibenzo[b,d]-pyran-1-ol (XIII) and 6a$\alpha$,7, 8, 10a$\beta$-tetrahydro-6,6,9-trimethyl-3-alkyl-(+)-6H-dibenzo[b,d] pyran-1-ol analogs (XI) were obtained.

The following Table summarizes the results of Test No. 6, relating to the reduction of body temperature due to the administration of compounds according to the present invention:

| Compound | Body Temperature Change in Mice (Test 6): 10mg/kg; in °C. - Change in °C. |
|---|---|
| III | unmeasurable due to psychotropic effect |
| IV | −3.0 |
| Xa | −2.7 |
| Va | −3.0 |
| Vb | −3.0 |
| XIa | −2.9 |
| XIb | −3.0 |

The pharmaceutical compositions of matter according to the present invention have a pronounced anti-asthmatic effect. Experiments on guinea pigs according to the method of Herxheimer, J. Physiol. 117=(1952) 251 have shown that when for example Compound V$_a$ is injected i.p., 10 mg/kg of animal weight, 1 hour in advance, 50 percent of asthma attacks are prevented.

The novel compounds according to the present invention have also a pronounced antipyretic effect and they have a pronounced analgesic effect. Experiments have shown that the compounds of the invention lower the body temperature of mice when examined according to the test procedure (6) set out on page 4. When 10 mg/kg were injected i.p. an average lowering of rectal temperature of 2.5° C. was obtained 30 minutes after injection. Several preliminary tests have shown the compounds according to the present invention to have an analgesic effect.

Existing hypertension in DOCA-saline treated rats was reversed by the application of 10 mg/kg/day of compound V$_a$. Hypertension was induced and when blood pressure had been raised to about 160 mm Hg from an average initial value of about 122 mm Hg, treatment was started. With control animals the blood pressure stayed high and decreased to about 155 mm Hg after 2 weeks. The blood pressure of the rats treated Table Summary of results

| Compound | Rotation $[\alpha]_D$ | Intestinal Motility (test 1) Dose mg/kg | Effect | Prevention of Hypertension (Test 2) Dose mg/kg | Effect % | Antiglaucomatic Effect (Test 3) % | CNS Action on mice (Test 4) Dose mg/kg | Effect % | CNS action (monkeys) (Test 5) Dose mg/kg | Effect | Ulcer prevention (test 7) Dose mg/kg |
|---|---|---|---|---|---|---|---|---|---|---|---|
| III (−) Δ$^1$ DMH | (−) | 30 | 0.12 | unmeasurable due to psychotropic effect | | 0.01 | 0.1 | 75 | 0.05 0.10 0.25 | ± + ++ | |
| IV (−) Δ$^6$ DMH | (−) | 30 | 0.17 | unmeasurable due to psychotropic effect | | 0.01 | 0.1 | 80 | 0.25 0.50 1.00 | − ++ +++ | |
| Xa | (+) | 30 | 0.25 | 10 | 50 | <0.001 | 10 | 17 | 1.0 2.5 10 | − − ± | |
| VA (+) Δ$^5$ THC DMH | (+) | 30 | 0.25 | 10 | 88 | <0.001 | 10 | 17 | 1.0 5.0 10.0 | − − + | 10 |
| Vb (+) Δ$^6$ THC 1.1 DMH | (+) | 30 | 0.18 | 10 | 95 | <0.001 | 10 | ·18 | 1.0 5.0 | − + | 10 |
| XIa (+) Δ$^1$ THC DMH | (+) | 30 | 0.17 | 10 | 90 | <0.001 | 10 | 14 | 1.0 2.0 5.0 | − − + | 10 |
| XIb (+) Δ$^1$ THC 1.1 DMH | (+) | 30 | 0.15 | 10 | 95 | <0.001 | 10 | 18 | 1.0 2.0 5.0 | − − + | 10 | decreased during 2 weeks to about 125 mm Hg. The experiment was evaluated statistically and it was found that the results are statistically highly significant.

The pharmaceutical compositions according to the present invention can be used in human medicine and in veterinary medicine. They can be administered in unit dosage form by the oral route. In this case tablets or capsules can be used. It is also possible to use solutions, emulsions or suspensions with suitable inert carriers. The pharmaceutical compositions can be applied topically in the form of lotions, creams or ointments comprising the active carrier in conjunction with suitable pharmaceutically acceptable carriers. The pharmaceutical compositions can be applied in the form of injections or infusions. They can be used in the form of ophthalmological preparations, such as eye-drops in a suitably buffered medium.

The unit dosage for human or veterinary use comprises generally from 10 mg to about 500 mg of the active ingredient in the form of tablets, lozenges or capsules. Solutions, emulsions or suspensions generally comprise from about 0.5 percent by weight to about 5 percent by weight of the active ingredient. Eye drops contain from about 0.5 percent to about 30 percent by weight of the active ingredient in a suitable buffered carrier. Pharmaceutical preparations in the form of lotions, creams or ointments generally contain from 0.1 percent to 10 percent by weight of the active ingredient in a suitable vehicle for topical application. Pharmaceutical compositions for injection or for infusion generally contain from 0.01 g to 5 g in unit dosage form in a suitable liquid medium or about 0.1 percent to about 2 percent solutions in a suitable liquid medium.

We claim:

1. A pharmaceutical composition of matter substantially devoid of "cannabis-type" CNS activity, comprising an amount sufficient to effectively treat pain, glaucoma, asthma or stomach or intestinal ulcers of, as active ingredient, a compound of the formula

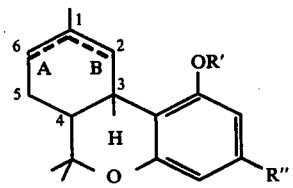

where A-----B designates a 1(2) or a 6(1) double bond and wherein R' designates —H or —CO—R where R is lower alkyl, and R" designates 1,1-dimethylheptyl or 1,2-dimethylheptyl, and a pharmaceutically acceptable excipient.

2. A pharmaceutical composition according to claim 1, wherein R" is 1,2-dimethylheptyl.

3. A pharmaceutical composition according to claim 1, wherein R" is 1,1-dimethylheptyl.

4. A pharmaceutical composition according to claim 1, wherein the double bond is in the $\Delta^6$-position.

5. A pharmaceutical composition of matter according to claim 1, in unit dosage form suitable for oral administration and comprising 10–500 mg of said active compound.

6. A pharmaceutical composition according to claim 1 for the treatment of glaucoma comprising 0.5–30% by weight of said active ingredient in a suitably buffered carrier.

7. A pharmaceutical composition according to claim 1 suitable for injection and comprising 0.1–2% of said active ingredient in a suitable liquid carrier.

8. A pharmaceutical composition according to claim 7 in unit dosage form containing from 0.01 g to 5 g of said active ingredient.

9. A compound having pharmaceutical activity but devoid of "cannabis-type" CNS activity of 3S,4S-configuration of the formula

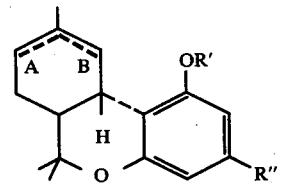

wherein A-----B designates a 1(2) or a 6(1) double bond,
R' designates —H or —CO—R where R is lower alkyl, and
R" designates 1,1-dimethyl-heptyl or 1,2-dimethylpeptyl.

10. A compound according to claim 9, wherein the double bond is in the $\Delta^6$-position and R" is 1,2-dimethylheptyl.

11. A compound according to claim 9, wherein the double bond is in the $\Delta^6$-position and R" is 1,1-dimethylheptyl.

12. A compound according to claim 9, wherein the double bond is in the $\Delta^1$-position and R" is 1,2-dimethylheptyl.

13. A compound according to claim 9, wherein the double bond is in the $\Delta^1$-position and R" is 1,1-dimethylheptyl.

14. A compound according to claim 9, the 5'-1,2- or 5'-1,1-dimethylheptyl homologue of (+)-(3S,4S)-$\Delta^6$-THC.

15. A compound according to claim 9, the 5'-1,2- or 5'-1,1-dimethylheptyl homologue of (+)-(3S,4S)-$\Delta^1$-THC.

* * * * *